United States Patent [19]
Lewandowski et al.

[11] Patent Number: 5,860,962
[45] Date of Patent: Jan. 19, 1999

[54] SHIELDED CANNULA FOR USE WITH AN I.V. SITE

[75] Inventors: Raymond D. Lewandowski, New Providence; Craig E. Widmaier, Red Bank, both of N.J.

[73] Assignee: Becton, Dickinson and Company, Franklin Lakes, N.J.

[21] Appl. No.: 986,433

[22] Filed: Dec. 8, 1997

[51] Int. Cl.$^6$ ............................................. A61M 5/00
[52] U.S. Cl. ............................................................... 604/263
[58] Field of Search ..................... 604/167, 169, 604/170, 187, 192, 199, 200, 201, 202, 206, 240, 241, 242, 243, 244, 256, 263, 264, 272, 280, 283, 905; 411/311, 310, 324, 412, 908; 285/333, 334, 355, 390

[56] References Cited

U.S. PATENT DOCUMENTS

| | | |
|---|---|---|
| D. 327,318 | 6/1992 | Dudar et al. |
| 4,734,002 | 3/1988 | Holmes ................................... 411/311 |
| 5,158,554 | 10/1992 | Jepson et al. ............................. 604/283 |
| 5,259,715 | 11/1993 | Harle ...................................... 411/311 |
| 5,295,657 | 3/1994 | Atkinson ................................. 604/256 |
| 5,405,340 | 4/1995 | Fageol et al. ............................ 604/241 |
| 5,620,427 | 4/1997 | Werschmidt et al. .................... 604/283 |
| 5,634,903 | 6/1997 | Kurose et al. ........................... 604/241 |
| 5,658,260 | 8/1997 | Desecki et al. ......................... 604/905 |
| 5,697,908 | 12/1997 | Imbert et al. ........................... 604/263 |
| 5,702,374 | 12/1997 | Johnson ................................. 604/283 |

*Primary Examiner*—Wynn Wood Coggins
*Assistant Examiner*—Sharon Finkel
*Attorney, Agent, or Firm*—John L. Voellmicke

[57] ABSTRACT

A shielded cannula for use with an I.V site having a threaded exterior surface and a septum comprises a cannula assembly including a hub having an open proximal end, a distal end, and a cavity therein, and a cannula having a proximal end projecting from the distal end of the hub, a distal end and a lumen therethrough in fluid communication with the cavity. A shield is connected to the cannula assembly and surrounds at least the proximal end of the cannula. The shield has a cylindrically shaped inside surface with at least one helical thread formed in the inside surface. A pointed plastic projection extends outwardly from the thread. The projection includes a base portion and a tip portion wherein the tip portion is positioned to be far enough away from the thread so that the tip portion is deflected by a thread on the exterior surface of the I.V. site when the thread of the shield engages the thread on the I.V. site.

11 Claims, 7 Drawing Sheets

SHIELDED CANNULA FOR USE WITH AN I.V. SITE

FIELD OF THE INVENTION

The subject invention relates to a shielded cannula for use in the delivery of medication or injectable liquid into an I.V. site having a septum, and more particularly, an I.V. site having a septum and thread engaging structure on its surface.

BACKGROUND

Medication or other injectable liquid in a syringe or other fluid handling device is frequently administered to a patient through an injection site of an intravenous set or catheter which is in fluid communication with a patient's vascular system. Injection sites or ports are covered by pierceable septums or pre-slit septums and are known in the art and sometimes referred to as "PRN" from the Latin pro re nata meaning "as the need arises." Pierceable septums are usually accessed by use of a sharpened cannula, such as a hypodermic needle which is used to pierce the septum and establish fluid communication with the catheter or I.V. set. There is a trend toward needleless I.V. systems which do not require a pointed cannula to pierce the injection site of an I.V. set. These systems have injection sites covered by a pre-slit septum which can be accessed with a blunt cannula. In some instances medication or other injectable liquid is administered to the I.V. set or catheter in a very short period of time such as one minute. In other instances, it is desirable to maintain the connection between the syringe or other fluid handling device for longer periods of time such as between two and seventy-two hours. Cannula, blunt or sharp, intended for longer term connection with the I.V. set or catheter are sometimes provided with some sort of retention structure to prevent the inadvertent disconnection of the cannula and the I.V. site. In the art, there are cannulas with levers which snap over portions of the I.V. site when the cannula enters the I.V. site. Removal requires the intentional flexure of the levers to unlock the fluid handling device from the I.V. site. Other prior art devices include shielded cannula with structure in the shield and cooperating structure in the cannula shield and on the I.V. site to provide for retention of the cannula in the septum of the I.V. site. Such structures included bayonet slots in the shield which engage pins on the I.V. site. With this structure, the operator is required to twist the shielded cannula after insertion of the cannula in the septum. Shielded cannula having internal threads in the shield are popular and intuitive to use. They can also shield the I.V. site during connection therewith to protect it from inadvertent contamination.

Threaded elements on the exterior of an I.V. site and on the interior of a cannula shield are tolerance sensitive. For example, shields, which have threads with peaks describing a diameter which is smaller than the root diameter of the thread on the I.V. site, may be impossible or difficult to engage and disengage. On the other hand, threads that are loose will engage easily and smoothly but may, in certain circumstances, tend to come loose. Such an occurrence will disconnect the medication or injectable liquid from the patient frustrating the patient's plan of therapy. Accordingly, although a threaded shielded cannula is a preferred device for connecting cannula to I.V. sites, there is still a need for a threaded shielded cannula which is less sensitive to manufacturing tolerances and provides high resistance to removal during the use of the product, and more preferably a higher resistance to removal than the resistance to insertion.

SUMMARY OF THE INVENTION

The subject invention relates to a shielded cannula for use with an I.V. site having a thread engaging structure on its exterior surface and a septum. The shielded cannula comprises a cannula including a hub having an open proximal end, a distal end and a cavity therein, and a cannula having a proximal end projecting from the distal end of the hub, a distal end and a lumen therethrough in fluid communication with the cavity. A shield is connected to the cannula assembly and surrounds at least the proximal end of the cannula. The shield has a cylindrically shaped inside surface with at least one helical thread, or portions thereof, formed in the surface. A pointed plastic projection extends outwardly from the thread. The projection includes a base portion and a tip portion with the tip portion being far enough away from the thread so that the tip portion is deflected by a threaded engaging structure on an exterior surface of an I.V. site when the thread of the shield engages the thread engaging structure on the I.V. site. The cannula may have a blunt distal tip or a sharp distal tip suitable for piecing the pierceable septum of an I.V. site. The shield may cover only the proximal end of the cannula or the proximal and the distal end of the cannula also. The projection may have numerous cross-sectional shapes including triangular and rectangular and extend along the full length of the thread or a short portion of the thread or be dispersed intermediately along the thread.

DETAILED DESCRIPTION

Figure 1:
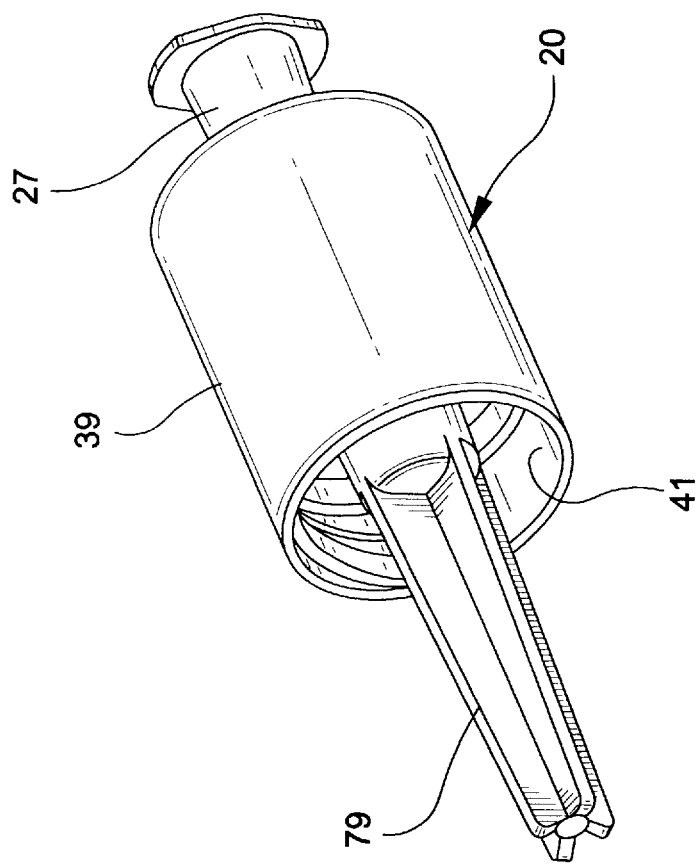
FIG. 1 is a side elevational view of the shielded cannula of the present invention with a protective cannula cover.
Figure 2:
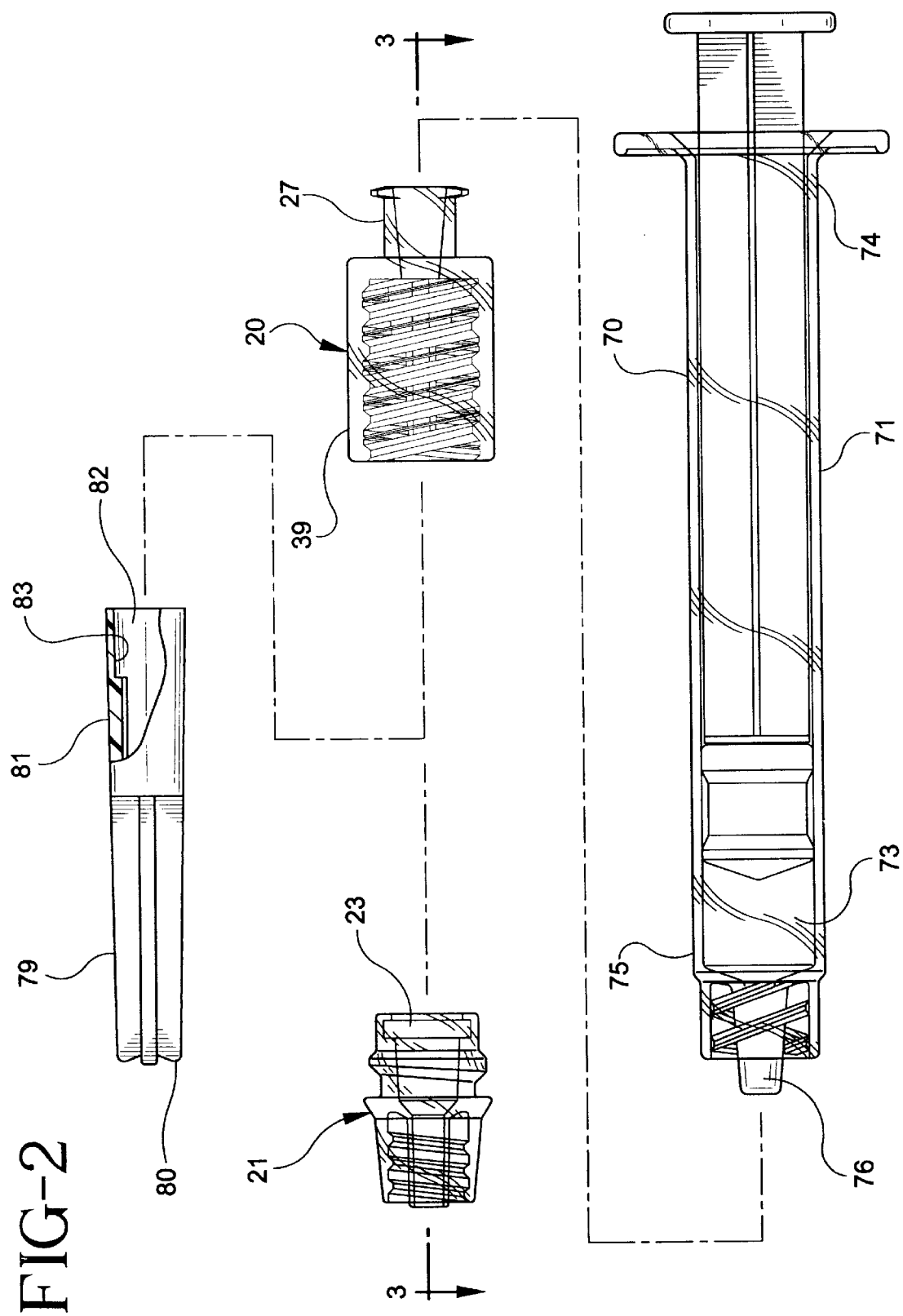
FIG. 2 is an exploded side elevational view of the shielded cannula, the cannula cover and I.V. site and a hypodermic syringe.

Referring to FIGS. 1–6, a shielded cannula 20, for use with an I.V. site 21 having thread engaging structure 22 on its exterior surface and a septum 23, comprises a cannula assembly 25 including a hub 27 having an open proximal end 28, a distal end 29 and a cavity 31 therein. Hub 27 also includes radial projections 32 on its proximal end to facilitate engaging a locking luer-type collar of a hypodermic syringe. A cannula 33 includes a proximal end 34 projecting from distal end 29 of the hub, a distal end 35 and a lumen 37 therethrough in fluid communication with cavity 31. In this embodiment, the distal end of the cannula includes a blunt tip 36.

A shield 39 is connected to cannula assembly 25 through radial projection 40. The shield surrounds at least a proximal end 34 of the cannula. The shield has a cylindrically shaped inside surface formed in inside surface 41. It is within the purview of the present invention to include multiple threads such as two and three pitch threads and threads that may not be continuous along the inside surface of the shield, for example, intermittent. Outside surface 44 of shield 39 is preferably, but not necessarily, cylindrically shaped. It is also preferable to have surface discontinuities on outside surface 44, such as longitudinal ribs, to help provide a surface which will not slip along the user's fingers during installation and removal of the cannula from the I.V. site or from a syringe or other fluid handling device.

A pointed plastic projection 51 extends outwardly from thread 43, preferably but not necessarily in substantially parallel relationship with the thread. Projection 51 includes a base portion 52 and a tip portion 53.

The shielded cannula of the present invention is intended for use with an I.V. site such as, but not limited to, I.V. site 21. I.V. site 21 includes a distal end 59 and a proximal end 60. Distal end 59 includes structure for connecting the site to an I.V. set or catheter which is in turn in fluid communication with the vascular system of a patient. I.V. sites can be integrally formed in a Y-site configuration wherein one branch of the Y communicates between a reservoir of I.V. fluid and a catheter inserted into the patient's vein and the other side of the Y-site includes a pierceable septum or pre-slit septum allowing for further introduction of medication or injectable liquids into the patient through the existing setup. The I.V. site illustrated is representative of these many combinations. Septum 23 of I.V. site 21 is pre-slit having a slit 24 in the septum. Thread engaging structure 21 on I.V. site 21 includes, thread 62 having a root 63, a peak 64 and sidewall 65.

Figure 3:
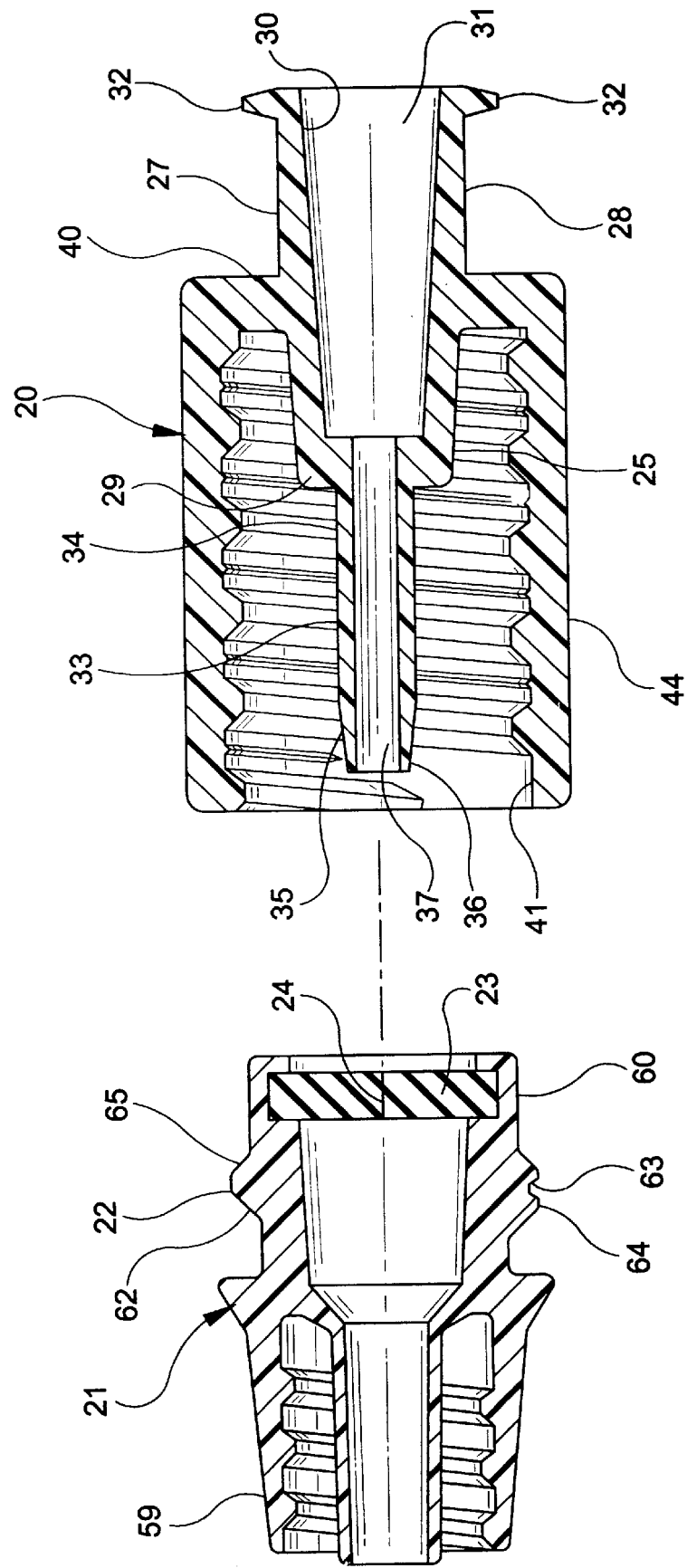
FIG. 3 is an enlarged cross-sectional view of the I.V. site and the shielded cannula of FIG. 2 taken along line 3—3.
Figure 6:
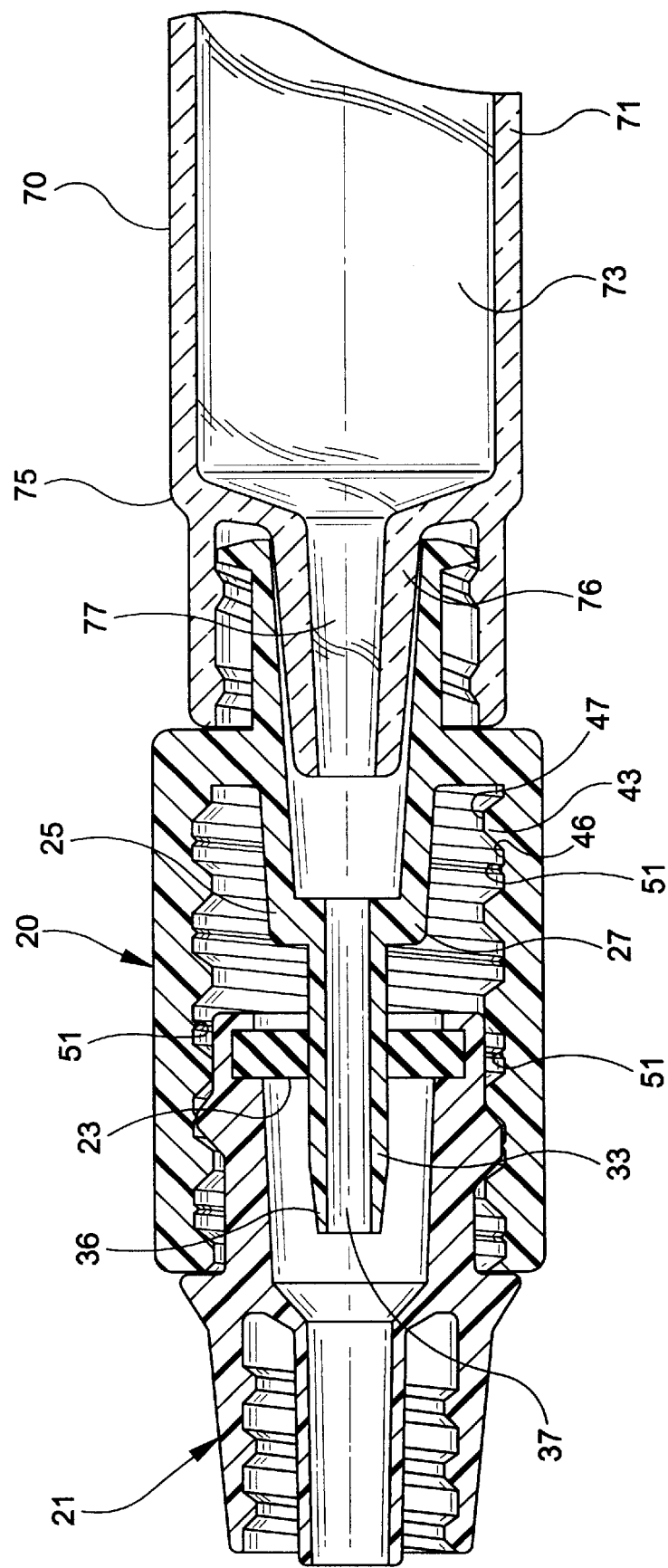
FIG. 6 is a cross-sectional view illustrating the shielded cannula, the I.V. site and a syringe barrel all assembled for the purpose of delivering injectable liquid from the syringe to the I.V. site.

Thread 43 formed in the inside surface of shield 39 includes a root 46, peak 47 connected by thread sidewalls 49. When the shielded cannula engages the I.V. site, thread engaging structure 21 will engage the helical thread 43 so that the peak 64 on the I.V. site thread will be near root 46 of the cannula thread and peak 47 of the cannula thread will be adjacent to root 63 of the I.V. site thread engaging structure, as best illustrated in FIG. 3 and FIG. 6.

An important feature of the present invention includes structure for helping to prevent inadvertent unscrewing of the shielded cannula from the I.V. site. To achieve this result the present invention provides a plastic projection which in this preferred embodiment is illustrated as 51 with base portion 52 and tip portion 53. The plastic projection in this embodiment is triangularly shaped. In use, it is preferred that the root diameter of the thread of the shield be slightly larger than the peak diameter of the thread engaging structure in the I.V. site so that extreme interference and high engagement forces are not encountered. However, the pointed plastic projection defines a diameter at its tip which is less than the diameter defined by the peak of the thread on the I.V. site so that installation of the shielded cannula to the I.V. site bends and deflects the pointed plastic projection. Samples of the present invention made in this configuration having a shielded cannula root diameter of about 9.8 mm (0.386 inch) with a base portion having a width of about 0.20 mm (0.008 inch) and a tip portion being extended about 0.20 mm (0.008 inch) from the base having a nominal interference of about 0.18 mm (0.007 inch), used, in conjunction with an I.V. site made of a thermoplastic such as polyester material, exhibited increased installation torque but more importantly the break-out torque to remove the shielded cannula from the I.V. site increased 15 to 20% within about 15 minutes after installation. Although it is not sure whether this increase will be maintained indefinitely, it has been shown to remain for approximately 72 hours, which is believed to be around the maximum time such connection will be used. It is theorized that the pointed plastic projection compresses and to some extent deflects, like an automobile windshield wiper blade, and upon deflection it tends to return toward its original shape therefore applying the additional force which is measured in the additional break-out torque about 15 minutes after installation.

Figure 5:
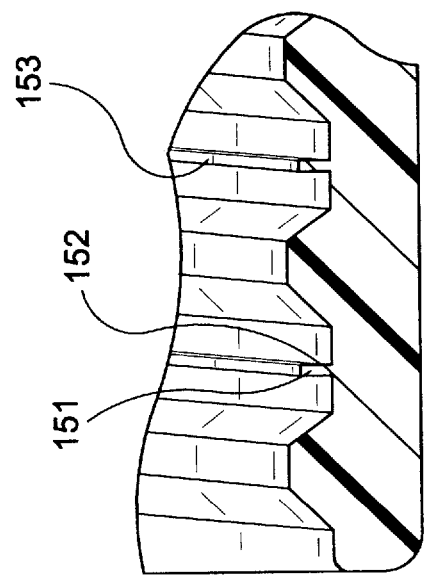
FIG. 5 is an enlarged cross-sectional view similar to FIG. 4 showing an alternative configuration for the pointed projection.
Figure 4:
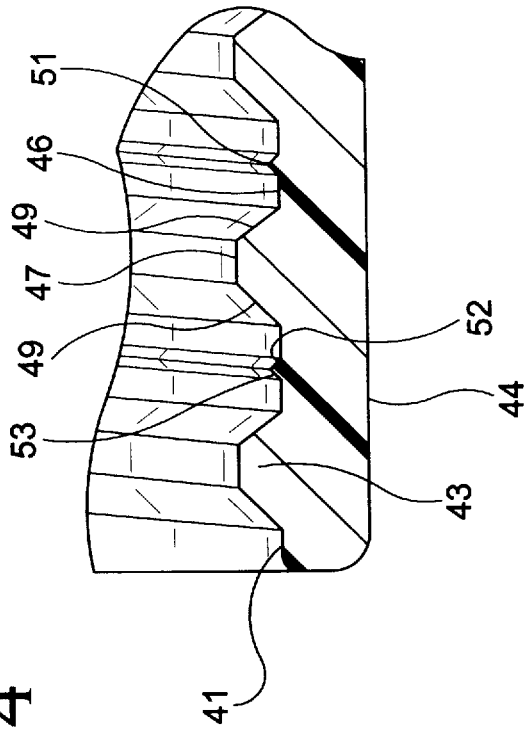
FIG. 4 is an enlarged view of the thread and pointed projection in the collar of the shielded cannula of FIG. 3.

An alternate embodiment of the pointed plastic projection is illustrated in FIG. 5. In this embodiment pointed plastic projection 151 includes a base portion 152 and a tip portion 153. Pointed plastic projection 151 is rectangularly shaped. This structure, although more difficult to manufacture, is believed to be capable of providing equal or superior results over the triangularly shaped plastic projection 51.

Although the pointed plastic projection of the invention is illustrated, in the preferred embodiment, as projecting from the root of the helical thread, it is within the purview of this invention to, as will be explained in more detail hereinafter, project from the peak of the thread or from the sidewalls.

It is expected that the shielded cannula of the present invention will frequently be used in conjunction with a hypodermic syringe having a syringe barrel 70 including an elongated cylindrical body 71 defining a chamber 73 for retaining fluid. The barrel includes an open proximal end 74, a distal end 75 and a tip 76 extending from the distal end and having a tip passageway 77 therethrough in fluid communication with the chamber. In use, the tip 76 is positioned within the open proximal end of hub 27 so that the chamber in the syringe barrel is in fluid communication with the lumen of the cannula, as illustrated in FIG. 6. Most syringes have a frusto-conically shaped tip. Accordingly, cavity 31 in hub 27 of this embodiment includes a frusto-conically shaped interior surface 30 suitable for frictionally engaging the frusto-conically shaped tip of a syringe barrel.

Shielded cannula preferably, but not necessarily, includes an elongated cannula cover 79 having a distal end 80, an open proximal end 81 and a hollow interior 82 having an interior surface 83. The cannula cover is removably mounted on the cannula assembly so that the distal end of the cannula is within the hollow interior of the cannula cover. It is preferred that the interior surface of the open proximal end of the cannula cover engages the distal end of the hub of the cannula assembly so that the hollow interior of the cannula cover surrounds the cannula without touching the cannula.

In use, a syringe is filled with medication or other injectable liquid using known sterile and clean techniques. After filling, the shielded cannula with cannula cover installed is mounted on the distal end of the syringe barrel so that hollow cavity 31 of hub 27 engages tip 76 on syringe barrel 70. Cannula cover 79 is now removed from the shielded cannula and the syringe and shielded cannula assembly is engaged with an I.V. site, as illustrated in FIG. 6. In the case of the blunt cannula, when the shielded cannula is screwed onto the I.V. site, the distal blunt tip 36 of the cannula forces its way through the slit in the pre-slit septum establishing fluid communication between chamber 73 of syringe barrel 70 and lumen 37 of cannula 33 so that the contents of the syringe may be dispensed through the syringe tip and the lumen of the cannula into the I.V. site. If only part of the contents of the syringe is dispensed into the I.V. site, the connected syringe may remain until such time as additional medication or other injectable liquid is needed. Further, the shielded cannula of the present invention can be connected to other fluid handling devices such as an I.V. line containing I.V. fluid for dispensing into the I.V. site and into the patient.

Figure 7:
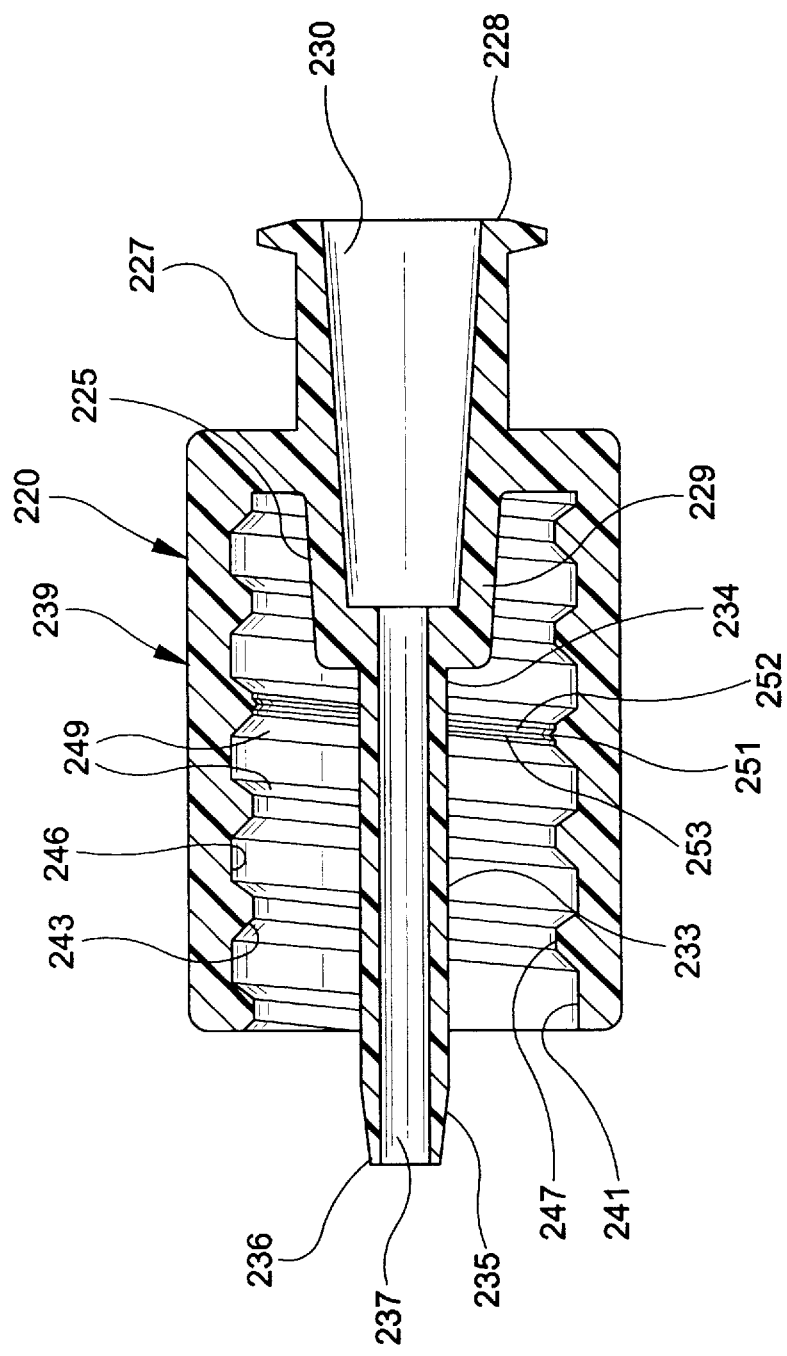
FIG. 7 is an alternative embodiment of the shielded cannula of the present invention.

FIG. 7 illustrates an alternate embodiment of the present invention wherein a shielded cannula 220 includes a cannula assembly 225 comprising a hub 227 having an open proximal end 228, a distal end 229 and a frusto-conically shaped cavity 230 therein. A cannula 233 having a proximal end 234 projecting from the distal end of the hub, a distal end 235 having a blunt tip 236 and a lumen 237 therethrough. A shield 239 is connected to the cannula assembly and surrounds the proximal end of the cannula but not blunt distal tip 236 of the cannula which projects outwardly from the distal end of the shield. The shield includes a cylindrically shaped inside surface 241 with at least one helical thread 243 formed in the inside surface. The thread includes a root 246, a peak 247 and sidewalls 249 therebetween. A pointed plastic projection 251 extends outwardly from peak 247 of thread 243 and is preferably in substantial parallel relationship with the thread. The projection includes a base portion 252 and a tip portion 253. As with the embodiments of FIGS. 1–6, the tip portion of the projection is positioned to be far enough away from the thread so that the tip portion is deflected by a thread engaging structure on the exterior of an I.V. site when the thread of the shielded cannula engages the thread engaging structure on the I.V. site. In this embodiment, the plastic projection is on the peak of the thread rather than on the root of the thread and extends only for about 180° along the thread rather than the full length of the thread as in the embodiments of FIGS. 1–6. The plastic projection can be continuous throughout the thread or through a short distance along a thread such as 180° or it can be intermittently placed along the thread so long as the plastic projection engages the threaded structure on the I.V. site when the cannula has passed through the septum and is in fluid communication with the interior of the I.V. site. In this embodiment, the cannula assembly and shield are integrally formed of thermoplastic materials such as polypropylene. The cannula assembly can be integrally formed of thermoplastic material and connected to a separate shield, and, in the alternative, the shield and the hub can be integrally formed with thermoplastic material with a separate cannula, such as a steel cannula, being attached to the hub.

Figure 8:
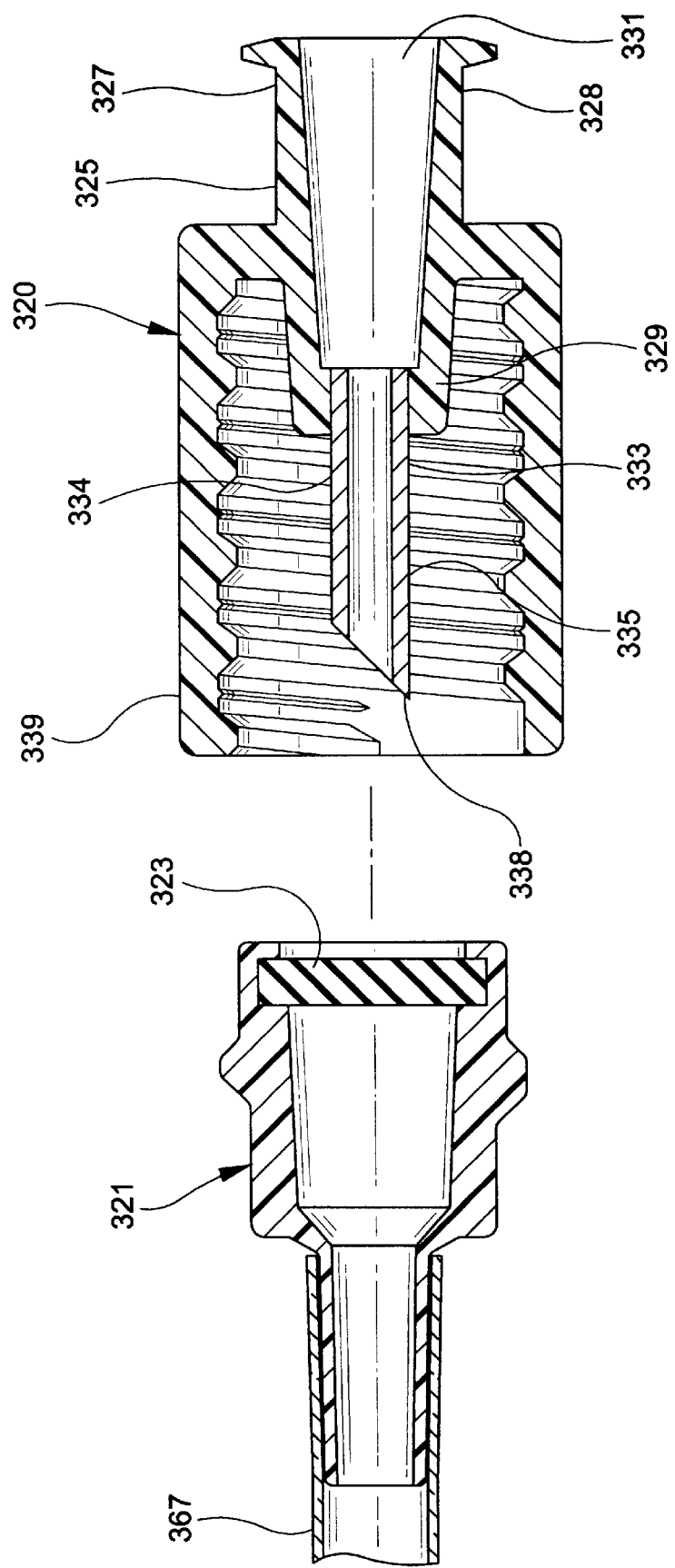
FIG. 8 is another alternative embodiment of the shielded cannula of the present invention.

FIG. 8 illustrates another alternative embodiment of the present invention wherein shielded cannula 320 comprises a cannula assembly 325 including a hub 327 having an open proximal end 328, a distal end 329 and a cavity 331 therein. A cannula 333 includes a proximal end 334 projecting from the distal end of the hub and a distal end 335 having a sharp distal tip 338 suitable for piecing the pierceable septum of an I.V. site such as I.V. site 321 having septum 323. I.V. site 321 is connected to tube 367 which may be a catheter or part of an I.V. set for delivering medication or other injectable liquid to a patient's vascular system. In this embodiment, the cannula 333 is preferably made of metal such as stainless steel and is held to the hub through adhesives, such as epoxy, or other suitable means. In this embodiment, the hub and shield 339 are integrally molded of plastic material such as polypropylene. In other respects, the shielded cannula 320 of this embodiment functions similarly to the shielded cannula of the embodiments of FIGS. 1–7 except that cannula 333 can be used with an I.V. site that does not have a pre-slit septum.

What is claimed is:

1. A shielded cannula for use with an I.V. site having a thread engaging structure on its exterior surface and a septum comprising:

a cannula assembly comprising a hub having an open proximal end, a distal end and a frusto-conically shaped cavity therein, a cannula having a proximal end projecting from the distal end of said hub, a distal end having a distal tip and a lumen therethrough in fluid communication with said cavity, a shield connected to said cannula assembly and surrounding at least said proximal end of said cannula, said shield having a cylindrically shaped inside surface with at least one helical thread formed in said surface, said thread comprising a root and a peak connected by thread sidewalls; and a pointed plastic projection extending outwardly from said root of said thread and in substantial parallel relationship with said thread, said projection including a base portion and a tip portion, said projection having a triangular-shaped cross section, said tip portion of said projection being far enough away from said thread so that said tip portion is deflected by a thread engaging structure on an exterior surface of an I.V. site when said thread on said shield engages the thread engaging structure on the I.V. site and said cannula is within a septum of the I.V. site.

2. The shielded cannula of claim 1 wherein said cannula, said hub and said shield are integrally formed of thermoplastic material.

3. The shielded cannula of claim 1 further including an elongated cannula cover having a distal end, an open proximal end and a hollow interior, said cannula cover being removably mounted on said cannula assembly so that said distal end of said cannula is within said hollow interior of said cannula cover.

4. The shielded cannula of claim 1 wherein said projection extends for at least 180 degrees along said thread.

5. The shielded cannula of claim 1 wherein said distal tip of said cannula is blunt.

6. The shielded cannula of claim 1 wherein said distal tip of said cannula is sharp.

7. The shielded cannula of claim 1 wherein said distal end of said cannula is surrounded by said shield.

8. The shielded cannula of claim 1 wherein said cannula is formed of metal.

9. The shielded cannula of claim 1 wherein said hub and said shield are integrally formed of thermoplastic material.

10. The shielded cannula assembly of claim 1 wherein said shield includes a cylindrically shaped outside surface substantially concentric with said inside surface.

11. The shielded cannula of claim 1 further including a syringe barrel having an elongated cylindrical body defining a chamber for retaining fluid, an open proximal end, a distal end and a tip extending from said distal end having a tip passageway therethrough in fluid communication with said chamber, said tip being positioned within said open proximal end of said hub so that said chamber is in fluid communication with said lumen of said cannula.

* * * * *